US007695507B2

(12) United States Patent
Rivelli, Jr. et al.

(10) Patent No.: US 7,695,507 B2
(45) Date of Patent: *Apr. 13, 2010

(54) NEUROVASCULAR STENT AND METHOD

(75) Inventors: Patrick Rivelli, Jr., Palo Alto, CA (US);
Alec Piplani, San Jose, CA (US); Sean Donahue, Halg Moon Bay, CA (US);
Alexander Leynov, Walnut Creek, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 895 days.

This patent is subject to a terminal disclaimer.

(21) Appl. No.: 11/393,200

(22) Filed: Mar. 30, 2006

(65) Prior Publication Data

US 2006/0224230 A1 Oct. 5, 2006

Related U.S. Application Data

(63) Continuation of application No. 09/715,878, filed on Nov. 17, 2000, now Pat. No. 7,037,330.

(60) Provisional application No. 60/241,101, filed on Oct. 16, 2000.

(51) Int. Cl.
*A61F 2/06* (2006.01)
(52) U.S. Cl. ............... 623/1.16; 623/1.11; 623/1.17; 623/1.18; 623/1.2
(58) Field of Classification Search ............... 623/1.15, 623/1.16, 1.17, 1.11–1.2
See application file for complete search history.

(56) References Cited

U.S. PATENT DOCUMENTS

| 4,580,568 | A | 4/1986 | Gianturco | 128/345 |
|---|---|---|---|---|
| 4,830,003 | A | 5/1989 | Wolff et al. | 128/343 |
| 4,955,889 | A | 9/1990 | Van Gent | 606/107 |
| 5,292,331 | A | 3/1994 | Boneau | 606/198 |
| 5,389,106 | A | 2/1995 | Tower | 606/198 |
| 5,443,498 | A | 8/1995 | Fontaine | 623/1 |
| 5,597,378 | A * | 1/1997 | Jervis | 606/78 |
| 5,707,386 | A | 1/1998 | Schnepp-Pech et al. | 606/194 |

(Continued)

FOREIGN PATENT DOCUMENTS

EP 0 717 961 A1 6/1996

(Continued)

*Primary Examiner*—Todd E Manahan
*Assistant Examiner*—Jennifer L Hornberger
(74) *Attorney, Agent, or Firm*—Vidas, Arrett & Steinkraus (57) ABSTRACT

A stent designed for catheter delivery to a target neurovascular site via a tortuous path, in a contracted state, and deployment at the target site, in an expanded state, is disclosed. The stent includes a plurality of expandable tubular members, where member is composed of a continuous wire element forming a plurality of wave segments, and segment contains a pair of opposite looped peaks having a wave shape such that the distance between adjacent sides of a wave, on proceeding from a peak toward opposite peaks, increases monotonically with an inflection point therebetween. The expandable tubular members are joined through adjacent peaks by axial connectors. Radial expansion of the stent from a contracted to expanded state is accommodated by movement of adjacent wave-segment peaks away from one another, without significant change in the axial dimension of the stent. Also disclosed are a system incorporating the stent, and a method of treating a neurovascular abnormality.

29 Claims, 7 Drawing Sheets

U.S. PATENT DOCUMENTS

| | | | |
|---|---|---|---|
| 5,755,776 A | 5/1998 | Al-Saadon | 623/1 |
| 5,817,152 A | 10/1998 | Birdsall et al. | 623/1 |
| 5,843,117 A | 12/1998 | Alt et al. | 606/194 |
| 5,843,175 A * | 12/1998 | Frantzen | 623/1.15 |
| 6,059,813 A | 5/2000 | Vrba et al. | 606/198 |
| 6,129,755 A | 10/2000 | Mathis et al. | |
| 6,132,460 A | 10/2000 | Thompson | 623/1.15 |
| 6,156,062 A | 12/2000 | McGuinness | 623/1.11 |
| 6,190,406 B1 | 2/2001 | Duerig et al. | |
| 6,325,826 B1 * | 12/2001 | Vardi et al. | 623/1.35 |
| 6,358,274 B1 | 3/2002 | Thompson | 623/1.15 |
| 6,419,692 B1 | 7/2002 | Yang et al. | |
| 6,464,720 B2 | 10/2002 | Boatman et al. | 623/1.15 |
| 6,673,106 B2 | 1/2004 | Mitelberg et al. | 623/1.2 |
| 6,860,899 B1 | 3/2005 | Rivelli, Jr. | 623/1.22 |
| 6,960,228 B2 | 11/2005 | Mitelberg et al. | 623/1.2 |
| 7,001,422 B2 | 2/2006 | Escamilla et al. | 623/1.12 |
| 7,037,330 B1 | 5/2006 | Rivelli, Jr. et al. | 623/1.15 |
| 7,037,331 B2 | 5/2006 | Mitelberg et al. | 623/1.15 |
| 2001/0044648 A1 * | 11/2001 | Wolinsky et al. | 623/1.15 |

FOREIGN PATENT DOCUMENTS

| | | |
|---|---|---|
| EP | 0 947 180 A2 | 10/1999 |
| WO | 00/00104 | 1/2000 |
| WO | WO 00/35378 | 6/2000 |
| WO | 02/34163 A3 | 5/2002 |

* cited by examiner

NEUROVASCULAR STENT AND METHOD

This application is a Continuation Application of and claims priority to U.S. application Ser. No. 09/715,878 file Nov. 17, 2000, now U.S. Pat. No. 7,037,330, which claims the benefit of U.S. Provisional Patent Application Ser. No. 60/241,101, filed on Oct. 16, 2000, both of which are expressly incorporated in their entireties herein by reference.

FIELD OF THE INVENTION

The present invention relates to a vascular endoprosthesis, such as a stent, for placement in an area of a body lumen that has been weakened by damage or disease such as by aneurysm, and in particular, to a stent adapted for placement at a neurovascular site, and to a method of using the stent in treating a neurovascular aneurysm.

BACKGROUND OF THE INVENTION

Rupture of non-occlusive cerebrovascular lesions, such as intracranial saccular aneurysms or arterio-venous fistulae, is a major cause of stroke. Rupture of an aneurysm causes subarachnoid hemorrhage in which blood from a ruptured vessel spreads over the surface of the brain. About 2.5% of the United States population (4 million Americans) have an unruptured aneurysm. About 100,000 of these people suffer a subarachnoid hemorrhage each year. The disease is devastating, often affecting healthy people in their 40's and 50's, with about half of the rupture victims succumbing within a month, and with half of the survivors becoming seriously disabled as a result of the initial hemorrhage or of a delayed complication.

Neurovascular arteries are generally quite small, having diameters ranging from 2.0 to 4.0 mm in the Circle of Willis, 2.5 to 5.5 mm in the cavernous segment of the internal carotid artery, 1.5 to 3.0 mm in vessels of the distal anterior circulation; and 2.0 to 4.0 mm in the posterior circulation. The incidence of aneurysm varies with the location, with 55% occurring in the Circle of Willis, 30% in the internal carotid, 10% in the distal anterior circulation, and 5% in the posterior circulation.

Screening for these lesions and preventing rupture will lead to heifer clinical outcomes and lower costs, Non-invasive treatments for ruptured and unruptured lesions are preferred over surgical interventions due to lower costs, lower mortality and morbidity, and patient preference.

One possible treatment for neurovascular aneurysms and other small vessel abnormalities involves placement of a stent at the site of weakened or damaged vessels. Such a treatment, however, involves several formidable challenges. First, assuming the stent is placed at the target site via a small-diameter catheter; the stent must be flexible enough to allow movement of the catheter along a typically tortuous vascular path, which may involve a number of sharp turns or bends in and through small-diameter vessels, i.e., vessels having diameters in the 2-8 mm range. Second, when the stent is released, it must be capable of expanding from the inner lumen diameter of the catheter to a diameter somewhat greater than that of the vessel at the target site, requiring an expansion ratio of at least twofold. Third, the stent must provide adequate structural support at the target site to maintain the vessel in a slightly expanded-diameter state. In particular the stent design should minimize the risk of metal fatigue as the stent is placed between its expanded and compressed forms. Fourth, the stent must provide a low profile and a surface that minimizes the formation of blood thrombi. Finally, the stent should provide an open-network skeleton that allows for delivery of additional agents, e g, vaso-occlusive coils, through the stent into the underlying aneurysm cavity.

Although a variety of intravascular stents have been proposed heretofore, for example, in U.S. Pat. Nos. 4,512,338, 4,503,569, 4,553,545, 4,795,485, 4,820,298, 5,067,957, 5,551,954, 5,562,641, and 5,824,053, none of these structures adequately meets the several requirements outlined above. In particular, the problem of providing a stent skeletal structure that has a contracted state diameter of 0.5-2 mm, is highly flexible in a contracted state, has a high expansion ratio on delivery from a catheter, and resists metal fatigue on expanding and contracting, has not been adequately solved heretofore.

It would therefore be valuable to provide an intravascular stent, particular one for use in treating neurovascular aneurysms and other vascular abnormalities, that provides the advantages and features mentioned above.

SUMMARY OF THE INVENTION

The invention includes, in one aspect, a stent designed for catheter delivery to a target neurovascular site via a tortuous path in a contracted state, and deployment at the target site in an expanded state. The stent includes a plurality of expandable tubular members, where each member is composed of a continuous wire element forming a plurality of wave segments, and each segment contains a pair of opposite looped peaks and has a wave shape such that the distance between adjacent sides of a wave in the stent's expanded state, on proceeding from a peak toward opposite peaks, increases monotonically with an inflection point therebetween. Adjacent tubular members are connected by axial connectors, preferably joining adjacent peaks of adjacent members, and preferably spaced from one another by intervening, unconnected confronting peaks. Radial expansion of the stent from a contracted to expanded state is accommodated by movement of adjacent wave-segment peaks away from one another, without significant change in the axial dimension of the stent.

In a preferred embodiment, the wire elements are formed of a NiTi shape memory alloy, and radial expansion is achieved by releasing the stent from such catheter. The stent of this embodiment may have a stress-induced martensite phase at body temperature, and/or an austenite phase transition temperature below body temperature.

Also in a preferred embodiment, the stent has a diameter; in its contracted state of between 0.5-2 mm, more preferably 0.71 mm to 1.65 mm, and an expansion ration of between 2 and 9, typically 3 and 6.

In another aspect, the invention includes a system for treating an aneurysm or other vascular abnormality in a neurovascular target vessel having an inner diameter less than about 8 mm and accessible via a tortuous vascular path. The system includes a guide wire that can be deployed at the target site, a catheter having a lumen inner diameter of 0.5 to 2 mm, and the above stent carried in its contracted state within the catheter's distal end region. The catheter and stent carried therein are adopted to be moved axially along the guide wire, for placing the catheter at the target site. Also included is a pusher wire movable through the catheter, for forcing the stent out of the catheter into the vascular site, where stent radial expansion is effective to lodge the stent at the target site. The pusher wire may be equipped with a distal-end stabilizer that is engageable with the stent when forcing the same from the catheter. Preferred stent features are given above.

In still another aspect, the invention includes a method of treating an aneurysm or other vascular abnormality in a neurovascular target vessel having an inner diameter less than about 8 mm and accessible via a tortuous vascular path. The method includes navigating a guide wire to the target site, and moving over the guide wire, a catheter having a lumen inner diameter of 0.5 to 2 mm, and the above stent carried in its contracted state within the catheters distal end region, until the catheter distal end is located at the target site. The guide wire is then replaced with a pusher wire, which is used to advance the stent out of the catheter into the vascular site, where stent radial expansion is effective to lodge the stent at the target site.

These and other objects and features of the invention will become more fully apparent when the following detailed description of the invention is read in conjunction with the accompanying drawings.

DETAILED DESCRIPTION OF THE INVENTION

Figure 1:
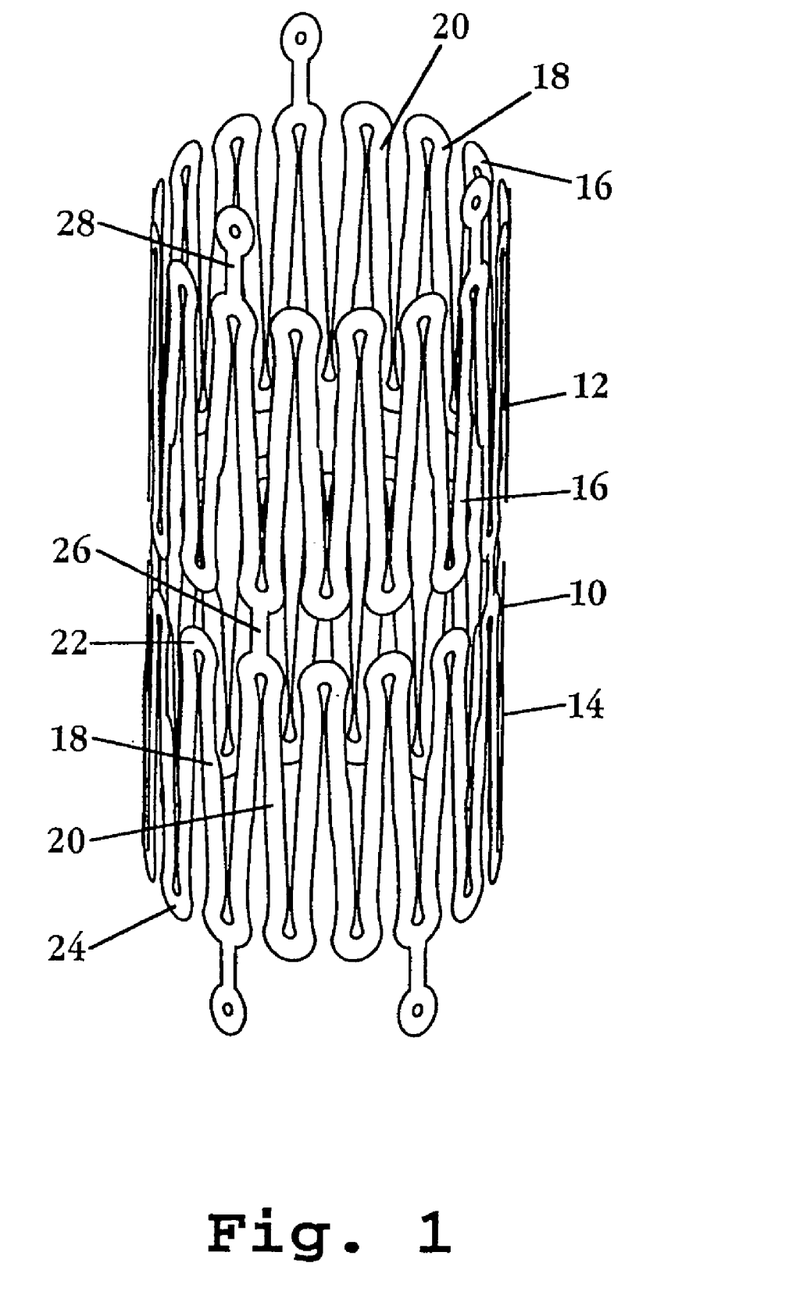
FIG. 1 is a side view of portions of a pair of connected tubular members forming the stent of the invention, and shown in a contracted state.
Figure 2:
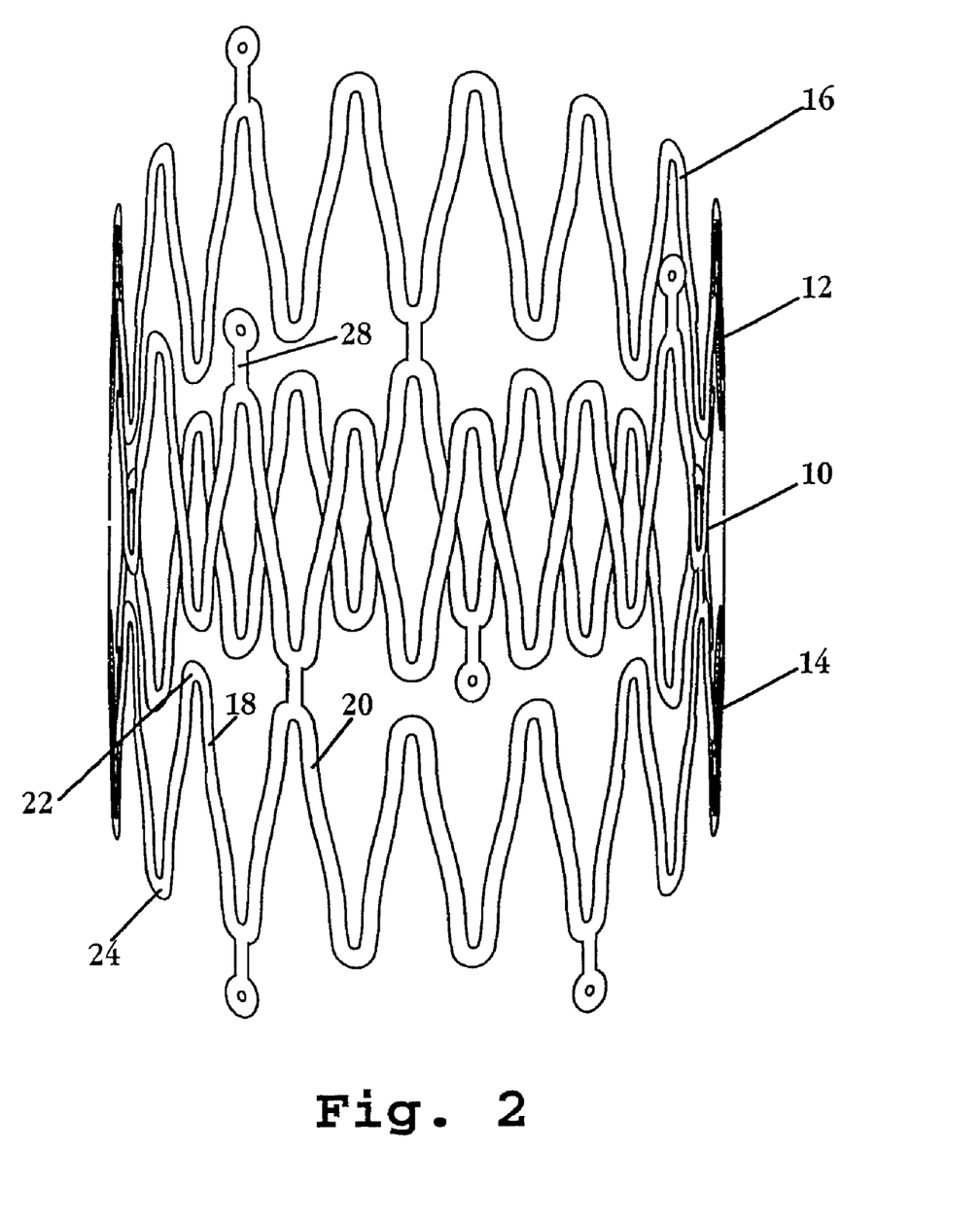
FIG. 2 shows the same tubular members in an expanded state.

FIGS. 1 and 2 show a portion of a stent 10 constructed in accordance with the invention, in the stent's contracted and expanded states, respectively. The stent includes a plurality of expandable tubular members, such as tubular members 12, 14. In actual construction, the stent may include many such members, e.g., 2-20, collectively forming an elongate cylindrical tube.

Each member of the stent is formed of a continuous wire element, such as wire element 16 in member 12, forming a plurality of wave segments, such as wave segments 18, 20 in member 14, whose shape and expansion characteristics will be described further below with respect to FIGS. 3-5. The wave segments have opposite looped peaks, such as looped peaks 22, 24 in wave segment 18. Adjacent tubular members are connected one to another by axial connectors, such as axial connector 26 joining members 14, 16, and axial connector 28 joining tubular member 12 to a third member (not shown). As seen, the axial connectors connect confronting peaks in adjacent members, although connections to other parts of the wave segments is contemplated. In a typical stent, the connectors are spaced from one another by at least one, and preferably three or four unconnected confronting peaks. That is, a majority of the confronting peaks are unconnected, providing greater stent flexibility in bending away from the stent long axis. Although the connectors shown here are simple linear connectors, the connectors may assume more complicated configurations, such as curved or zig-zag shapes which may themselves stretch to accommodate off-axis bending of the stent, providing greater flexibility.

Preferably, the stent has a contracted-state diameter (FIG. 1) of between 0.5-2 mm, more preferably 0.71 to 1.65 mm, and a length of between about 0.5-4 cm, composed of 2-20 tubular members, each about 0.25 to 1.0 mm in length. The axial connectors have a length typically of 3-20% that of the tubular members.

Each tubular member is composed of between 5-25 wave segments, defined as repeating segments of the associated wire elements, as described below with respect to FIGS. 3-5. In its expanded state, shown in FIG. 2, the stent diameter is at least twice and up to 8-9 times that of the stent in its contracted state. Thus, a stent with a contracted diameter of between 07 to 1.5 mm may expand radially to a selected expanded state of between 2-8 mm or more.

Figure 3:
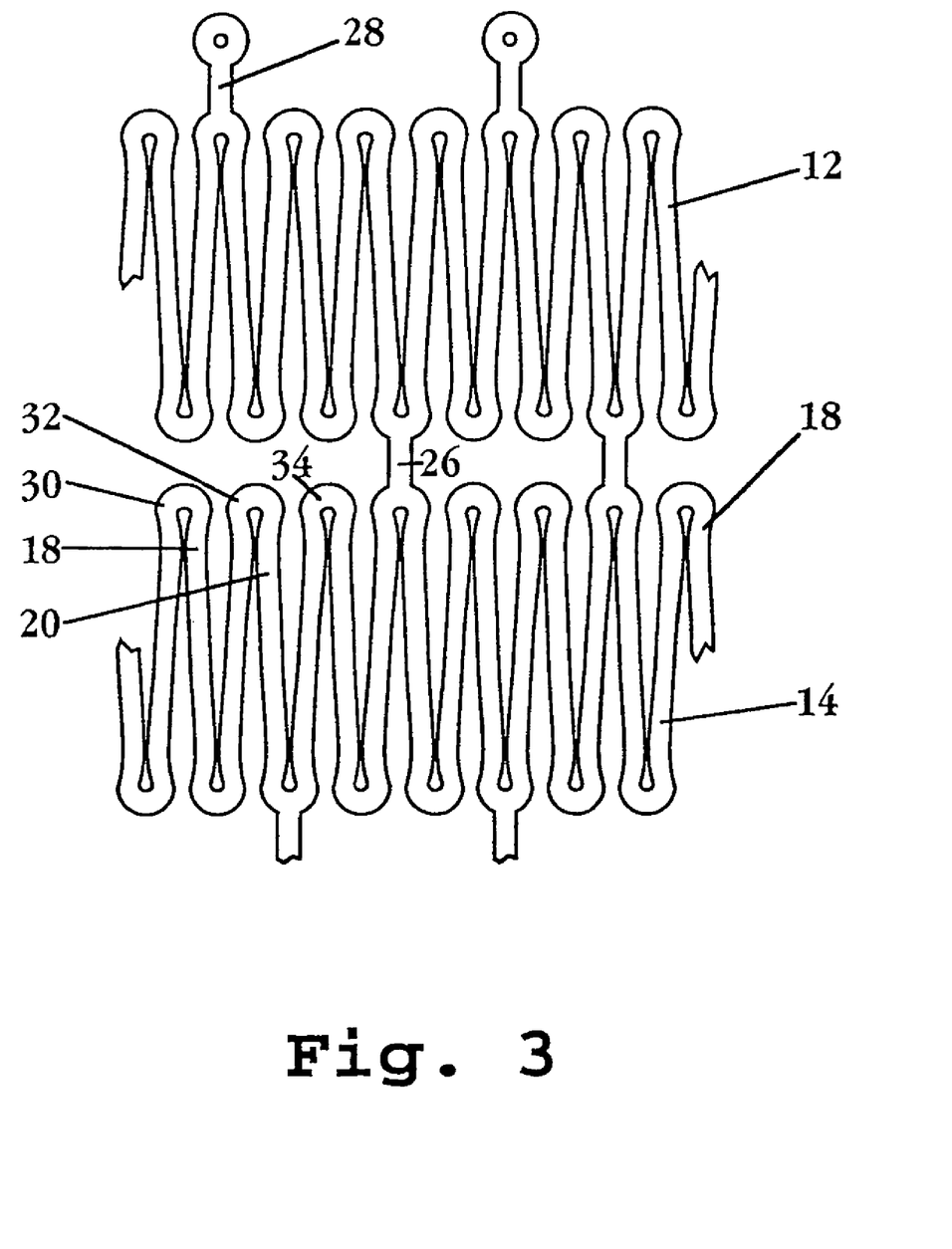
FIG. 3 shows a portion of a stent constructed according to the invention, in a contracted state.
Figure 4:
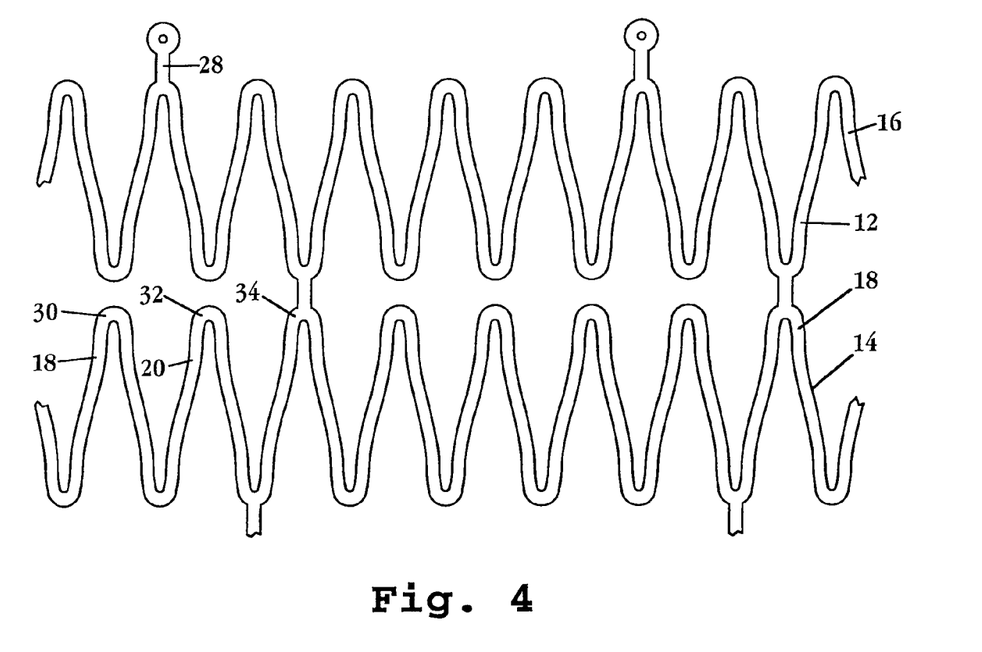
FIG. 4 shows the same portion of the stent, but in an expanded state.

The relationship between the shape of the wave segments in the tubular 25 methods and the mode of radial expansion of the stent is illustrated particularly in FIGS. 3 and 4, which show portions of the tubular members as they would appear if laid out in a plane. In particular, the figures show portions of tubular members 12, 14, each formed of a continuous wire element, such as wire element 18 forming member 14. Each wire element, in turn, is formed of a series of repeating-unit wave segments, such as wave segments 18, 20, where the "end" of one segment is the "beginning" of the next segment.

The "end/beginning" point of the wave segments, which occurs at the same phase point in each wave, is arbitrary, and for purposes of illustration is indicated at a point such as indicated at 30, 32, 34, which is near the top of the loop in the upper looped peak of each wave segment. Thus, wave segment 18 is defined as the portion of the wire element between points 30, 32, and segment 20, as the portion of the element between points 32, 34.

In the stent's contracted state, the wave segments are compressed closely together, as seen in FIG. 3, where adjacent looped peaks are in contact with one another or nearly in contact and the looped peaks are squeezed together. According to an important feature of the invention, the wave segments forming the wire element accommodate movement of the opposite arms of a wave segment, such as opposite arms 36, 38 in segment 18, away from one another, with relatively larger movement occurring in the center portion of the wave segment, i.e., the portion between opposite looped peaks.

Figure 5A:
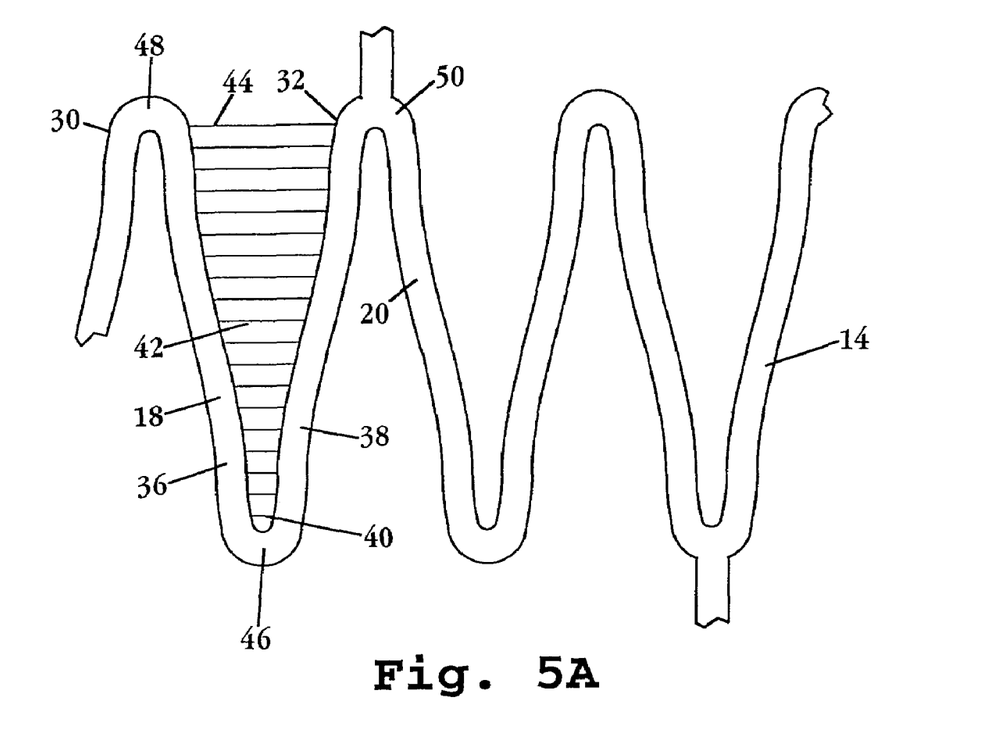
FIGS. 5A and 5B illustrate the change in distance between adjacent sides of a wave segment in a tubular member, on proceeding from a lower wave peak to the opposite (upper) side of member (5), and a plot this distance as a function of the peak-to-peak distance, showing the inflection point in the distance plot.
Figure 5B:
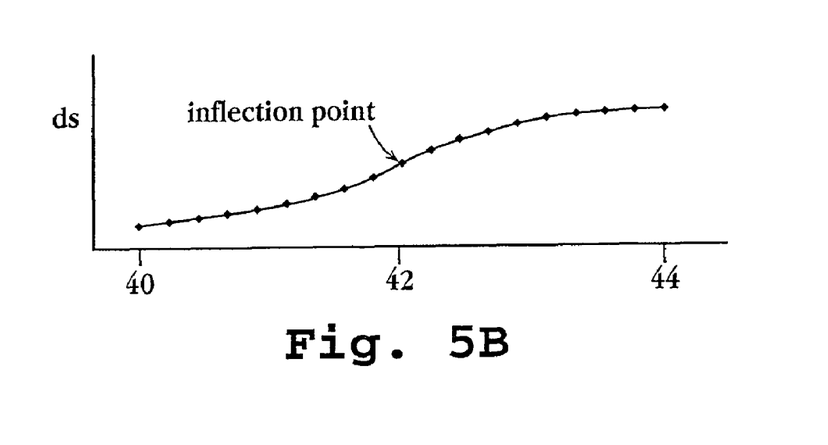

This feature is illustrated particularly in FIG. 5A, which shows three adjacent wave segments, including segment 18 in its expanded (or expanding) form. Distances between opposite sides 36, 38 of wave segment, such as distances 40, 42, 44, are shown for a number of points between looped peak 46 in segment 18 and opposite looped peaks 48 in segment 18 and 50 in adjacent segment 20. In the plot shown in FIG. 5B, the x-axis represents the distance from a peak in a wave segment, with the ordinates 40, 42, 44 in FIG. 5A shown. The distance along the y-axis represents the distance between opposite sides of the wave segment. As seen, the plot shows a relatively small slope ($\Delta x / \Delta y$) in the wave regions adjacent the peaks and the greatest slope in the center region of the segment between the looped peaks. The point of greatest slope, corresponding roughly to midpoint 42 between the peaks, is an inflection point in the plot, as the slope of the plot increases between points 40 and 42, and then begins to decrease between points 42 and 44. Further, with reference to FIGS. 1 and 3, the distance between opposite sides of a wave segment in the contracted state is at a minimum at a point intermediate the looped peaks, where opposite sides of a wave appear to be touching in the two figures.

At the same time, the element can undergo a severalfold radial expansion by virtue of the ability to be close packed in a contracted state (unlike a sin wave), and still provide significant expansion between wave segment arms. This is in contrast to a sin-wave wire element in which compression at the peaks, and thus the number of wave segments that can be accommodate in the contracted state, is limited.

Finally, and as can be appreciated from FIGS. 3 and 4, radial expansion of the stent produces little change in the overall length of the tubular members, preserving the overall stent length during deployment and expansion. The stent may be formed by conventional stent construction methods involving either initial formation of the individual tubular members, and subsequent attachment of one member to another by axial connectors, or by laser cutting a thin-walled tube to have the skeletal features making up the stent, as detailed below. In the former method, the wire element may be formed by shaping a wire segment and joining the wire ends to form the desired tubular member. In the latter case, the wire element is formed by cutting and removing portions of a cylindrical tube.

The stent preferably exhibits a relatively high degree of biocompatibility since it is implanted in the body. Where the stent is self-expanding, suitable stent materials include compressible, biocompatible polymers, ELGILOY (available from Carpenter Technology Corporation of Reading, Pa.) and PHYNOX (available from Metal Imphy of Imphy, France). Both of these metals are cobalt-based alloys which also include chromium, iron, nickel and molybdenum. Other materials for a self expanding stent include 316 stainless steel and MP35N alloy which are available from Carpenter Technology Corporation and Latrobe Steel Company of Latrobe, Pa., and superelastic Nitinol nickel-titanium alloy which is available from Shape Memory Applications of Santa Clara, Calif. Nitinol alloy contains about 45% titanium.

In one general embodiment, the stent is formed of a shape-memory alloy having a final austenite transition temperature of between about 25° C. and 37° C. This feature allows the stent to be carried in the catheter in a martensitic state, and assume its preformed, austenite shape when expelled from the catheter and exposed to the higher body temperature at the target site. In another embodiment the shape-memory alloy has a transition temperature $M_d$ greater than 37° C., below which the alloy retains sufficient stress-induced martensitic property to allow placement of the stent at or above its $A_f$. In other words, this allows the stent to be carried in the catheter in a stress-induced martensitic (SIM) state, and recover its preformed, austenitic shape when released from the constraints of the catheter, at a temperature that may be substantially above the final austenite temperature without significant plastic, or otherwise permanent deformation. In this embodiment, the final austenite temperature may be quite low, e.g., 4° C., or it may be room temperature or higher.

Nitinol cylindrical tubes having desired transition temperatures, as noted above, can be prepared according to known methods. In an exemplary method of manufacture of the stent having these properties, a nitinol hypotube, e.g., 8 mil wall thickness, is subjected to centerless grinding to a wall thickness of 3 mil. The stent pattern is cut by a laser (e.g., as described by Madou in Fundamentals of Microfabrication, CRC Press, 1997). Both inner and outer surfaces are polished to a mirror finish using electro-polish techniques (e.g., as described by Madou, 1997). A gold coat may be applied by ion beam assist or by sputtering. Alternatively, or additionally, a radio-opaque marker may be affixed to the stent to improve radio-opacity.

During manufacture, the stent is formed at the expanded condition (FIG. 2), 30 corresponding to the final deployed size (e.g. about 3-8 mm outer diameter), and heated to a temperature above the transition temperature. The stent is then subjected to thermoelastic martensitic transformation (e.g., as described in U.S. Pat. No. 5,190,546 incorporated by reference in its entirety herein) by cooling below the transition temperature range of the alloy and deformation to the contracted condition suitable for use within an intraluminal catheter. The transition temperature can be modified by varying the ratios of each metal in the alloy and in one embodiment, is preferably is within the range between about 25° C. to 45° C. at which the stent expands. A more preferred transition temperature range is between about 25° C. to 37° C. For example, the alloy can comprise 55% nickel, and 45% titanium which gives a transition temperature of about 32° C. to 33° C., which is below body temperature but above room temperature.

Nitinol cylindrical tubes having a martensite temperature $M_D$ below which the alloy can assume a stress-induced martensitic condition while being stressed to the extent necessary to place or otherwise use the device, of greater than about 37° C., preferably greater than about 40° C., are also prepared according to known methods, e.g., U.S. Pat. No. 4,505,767. For example an ideal alloy would act, at about 37° C., as a constant force spring over a strain range up to about 5% or more. This is a measurement of the degree to which an alloy, at a given temperature, can be strained in a purely austenitic state by the formation of stress-induced martensite without significant plastic deformation. In other words, the strain caused by the application of a given stress at a given temperature is substantially recoverable. In practice, the maximum stress realized occurs sometime during the process of placing a nitinol device at a given temperature. Accordingly, a suitable alloy will provide a device that is capable of substantially recovering its austenitic shape without significant plastic deformation, upon placement in the body.

Figure 6A:
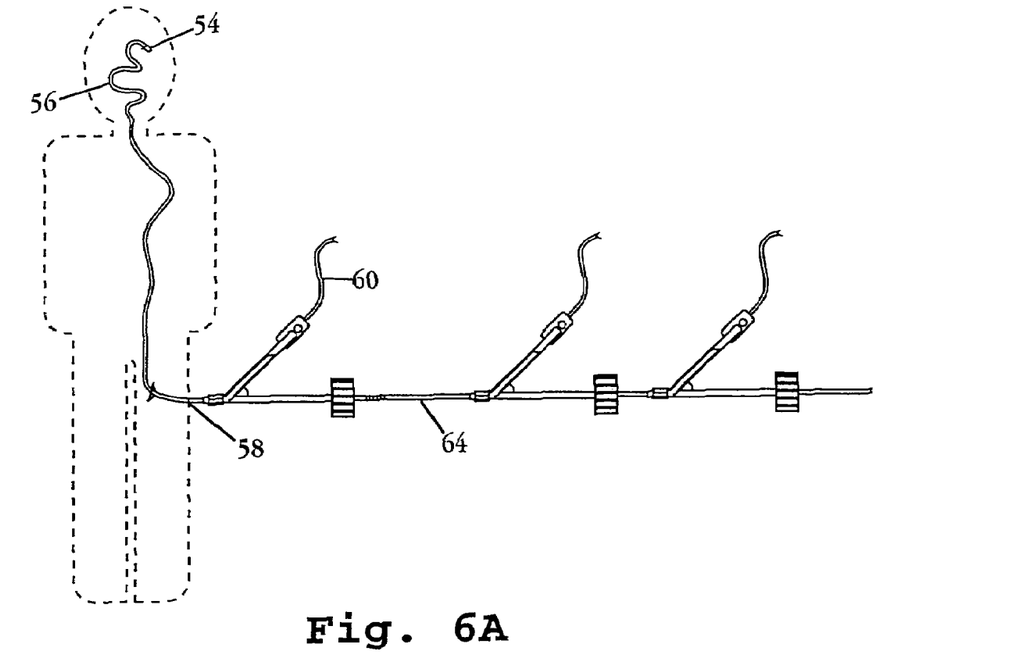
FIGS. 6A and 6B show various components of the system of the invention, in a stent-delivery method, and at two stages of stent delivery.

The method of placement of the stent, and a stent system for practicing the method will now be described with reference to FIGS. 6 and 7. The target site in the method is typically a neurovascular site, such as site 54, in the brain, which is accessible only via a tortuous vascular path 56, by which is meant a vascular path containing a plurality of bends or turns which may be greater than 90 turns, and involving vessels which are less than about 8 mm, and as small as 2-3 mm, in diameter.

Initially, a guide catheter 60 is placed at the target site according to known methods. Then the target site is accessed by a flexible guidewire (such as described in U.S. Pat. No. 4,619,274) and a flexible catheter 64. Once the target site is reached, the catheter tube is pulled out, leaving the flexible guidewire in place. The stent-delivery catheter 62, as seen in FIG. 68, is advanced over the guidewire until the target site is reached.

Figure 7A:
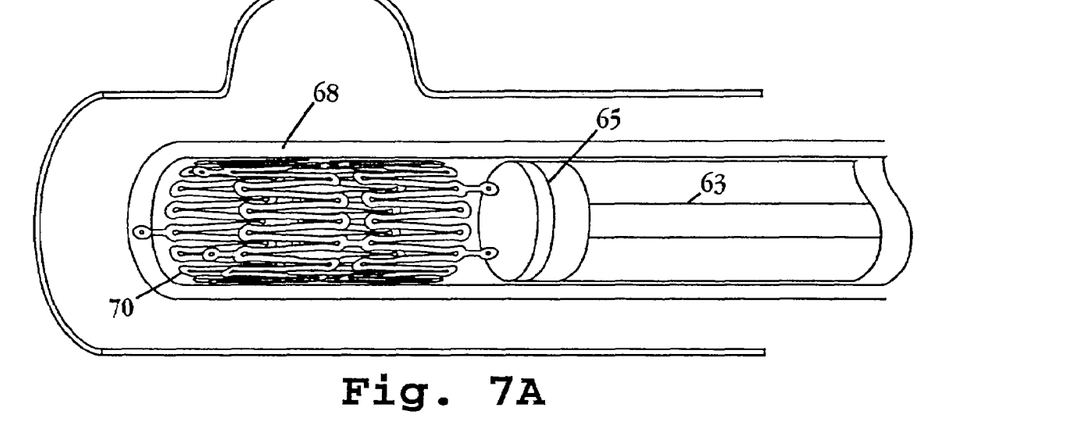
FIGS. 7A and 7B are expanded views of distal end portions of the system, of the invention, shown in relation to a vascular target site, just prior to release at the target site (7A) and after deployment at the site and stent expansion in the target vessel.

The distal end of stent-delivery catheter 62 is shown in FIG. 7A, and includes a catheter 68 having an inner lumen having a diameter preferably between about 0.5 to 2 mm, e.g. 0.71 to 1.65 mm. A stent 70 constructed in accordance with the invention is carried in its contracted state at the distal end of the catheter.

Figure 6B:
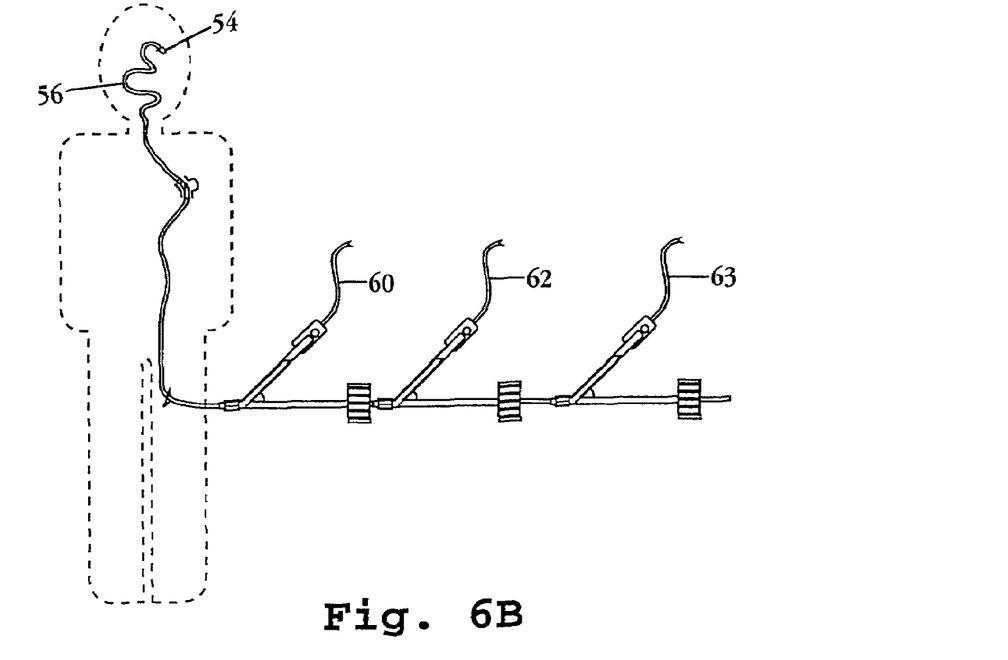
Figure 7B:
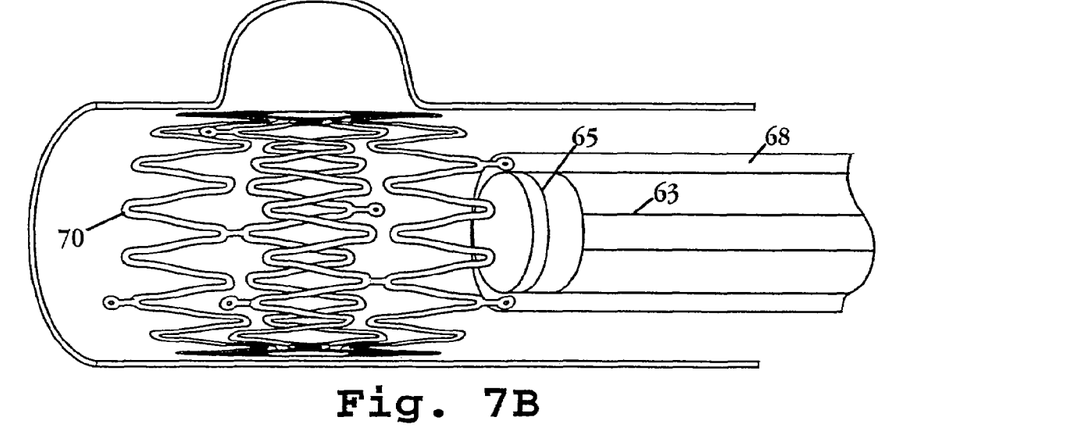

Once the stent-delivery catheter is in place, with its distal end at the target site, the guidewire is removed and replaced with a pusher wire 63 (as shown in FIG. 6B) having a distal-end stabilizer 65, which has a distal head surface dimensioned to engage the proximal end of the stent. To deploy the stent the pusher wire is advanced and pushed against the stent until the stent is pushed out of the catheter, as shown in FIG. 7B. Once released from the constraints of the catheter, the stent is free to self-expand to a diameter slightly greater than the diameter of the vascular site, thus locking the stent in place at the target site.

More specifically, the method of the invention includes navigating a guide wire to the target site, moving over the guide wire, a catheter having a lumen inner diameter of 0.5 to 2 mm and a distal end region in the lumen, and the stent of the invention, carried in its contracted state within the catheter's distal end region, until the catheter distal end is located at the target site. The guidewire is then replaced with a pusher wire, which is advanced within the catheter to force the stent out of the catheter into lodge the stent at the target site.

The system of the invention used in carrying out the method includes a guidewire that can be deployed at the target site, a catheter having a lumen inner diameter of 0.5 to 2 mm and a distal end region in the lumen, and adapted to be placed at the target site via such path, and the stent of the invention carried in its contracted state within the catheter's distal end region, where the catheter and stent carried therein are adapted to be moved axially along the guide wire, for placing the catheter at the target site. A pusher wire is movable through the catheter for forcing the stent out of the catheter into the vascular site, where stent radial expansion to its expanded state is effective to lodge the stent at the target site.

The stent and system employing the stent of the present invention can be used in the treatment of a variety of vascular lesions such as an aneurysm, fistula, occlusion, or narrowing and is particularly useful in treating targets located in tortuous and narrow vessels, for example in the neurovascular system, or in certain sites within the coronary vascular system, or in sites within the peripheral vascular system such as superficial femoral, popliteal, or renal arteries.

From the foregoing, it can be appreciated how various objects and features of the invention are met.

The axial construction Of the stent, composed of short tubular members joined by axial connections, and the ability of the joined members to flex radially, by distributed bending within the looped regions of the wire elements, allows the stent to be moved over high-angle, small-radius bends, with relatively little localized stress and metal fatigue.

The ability of the stent to be close-packed, in its contracted state, and have a smooth wave-like character in its expanded (and expanding) state, allows the stent to expand severalfold when deployed, with a minimum risk of metal fatigue due to concentrated stresses, or damage to the vessel wall, due to sharp points on the stent. In its expanded state, the stent provides good radial strength, for holding the stent in place.

The stent has a low profile, which may be in the 2-4 mil range for stent thickness, Finally, the stent should provide an open-network skeleton that allows for delivery of additional agents, e.g., vaso-occlusive coils, through the stent into the underlying aneurysm cavity.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit of scope of the appended claims.

It is claimed:

1. A stent having a contracted state and an expanded state, wherein the stent is expandable from its contracted state to its expanded state, comprising:
   a plurality of expandable tubular members,
   each expandable tubular member disposed about a longitudinal axis, having a proximal end and a distal end and comprising a plurality of wave segments, each wave segment containing a pair of opposite looped peaks, one of said pair of opposite looped peaks being at the distal end and the other of said pair of opposite looped peaks being at the proximal end, and adjacent sides and having a wave shape, such that, in the stent's contracted state, the distance between adjacent sides of the wave segment monotonically decreases to a minimum at a point along a portion of the wave segment extending from one of the pair of opposite looped peaks of the wave segment at one end of the expandable tubular member to the point along the wave segment and thereafter along the wave segment, extending from said point to the remaining looped peak of the pair of opposite looped peaks at the other end of the tubular member, the distance between the adjacent sides of the wave segment at any point is greater than the minimum, and such that, in the stent's expanded state, the distance between the adjacent sides of the wave segment on proceeding from one of the pair of opposite looped peaks toward the remaining looped peak of the pair of opposite looped peaks increases monotonically, wherein, when the monotonically increasing distance is plotted as a function of distance from the one of the pair of opposite looped peaks at one end of the segment along the wave segment, the resulting curve includes an inflection point; and
   axial connectors joining adjacent expandable tubular members.

2. The stent of claim 1, wherein radial expansion of the stent from its contracted to its expanded state is accommodated by movement of adjacent wave segment peaks away from one another, without significant change in the axial dimension of the stent.

3. The stent of claim 1, each expandable tubular member being composed of a continuous wire element.

4. The stent of claim 3, wherein the axial connectors are portions of the continuous wire element.

5. The stent of claim 4, wherein the stent is cut from a tube.

6. The stent of claim 1, wherein the axial connectors join one or more confronting peaks of adjacent tubular members.

7. The stent of claim 1, wherein the wire elements are formed of a NiTi shape memory alloy, and said radial expansion is achieved by releasing the stent from such catheter.

8. The stent of claim 7, which has a stress-induced martensite phase at body temperature.

9. The stent of claim 7, which has an austenite phase transition temperature below body temperature.

10. The stent of claim 1, wherein the axial connectors connecting adjacent expandable tubular members are attached to confronting peaks of the adjacent expandable tubular members, and the axial connectors are spaced from one another by intervening, unconnected confronting peaks.

11. The stent of claim 10, which can be carried in a distal end region of a catheter having a lumen inner diameter between about 0.5 and 2 mm, and adapted to be placed at the target site via a tortuous vascular path in the brain.

12. The stent of claim 1, wherein the stent in its contracted state has an inner diameter of between 0.5 and 2 mm, and the stent diameter in its expanded state is between 2-9 times that in its contracted state.

13. The stent of claim 1, wherein, in the stent's contracted state, the sides have at least two inflection points.

14. A system for treating a aneurysm or other vascular abnormality in a neurovascular target vessel, comprising a guide wire that can be deployed at the target site, a catheter having a lumen and a distal end region in the lumen, and adapted to be placed at the target site, the stent of claim 1 adapted to be carried in its contracted state within the catheter's distal end region, where the catheter and stent carried therein are adapted to be moved axially along the guide wire, for placing the catheter at the target site, and a pusher wire movable through the catheter, for forcing the stent out of the catheter into the vascular site, where stent radial expansion to its expanded state is effective to lodge the stent at the target site.

15. The system of claim 14, which further includes a stabilizer attached to the distal end of the pusher wire, engageable with the stent when forcing the same from the catheter.

16. The system of claim 14, wherein the neurovascular target vessel has an inner diameter less than about 8 mm.

17. The system of claim 14, the catheter having a lumen inner diameter of 0.5 to 2 mm.

18. The system of claim 14, wherein the stent in its contracted state has an inner diameter of between 0.5 and 2 mm, and a diameter in the expanded state of between 2-9 times that in the contracted state.

19. A method of treating an aneurysm or other vascular abnormality in a neurovascular target vessel, comprising:

navigating a guide wire to the target site, moving over the guide wire, a catheter having a lumen and a distal end region in the lumen, and a stent carried in a contracted state within the catheter's distal end region, until the catheter distal end is located at the target site, and being formed of (i) a plurality of expandable tubular members, each expandable tubular member disposed about a longitudinal axis, having a proximal end and a distal end and comprising a plurality of wave segments, each segment containing a pair of opposite looped peaks, one of said pair of opposite looped peaks being at the distal end and the other of said pair of opposite looped peaks being at the proximal end, and adjacent sides and having a wave shape, such that, in the stent's contracted state, the distance between the adjacent sides of the wave segment monotonically decreases to a minimum at a point along a portion of the wave segment extending from one of the pair of opposite looped peaks of the wave segment at one end of the expandable tubular member to the point along the wave segment and thereafter along the wave segment, extending from said point to the remaining extending from said point to the remaining looped peak of the pair of opposite looped peaks at the other end of the tubular member, the distance between the adjacent sides of the wave segment at any point is greater than the minimum, and such that, in the stent's expanded state, the distance between the adjacent sides of the wave segment on proceeding from one of the pair of opposite looped peaks toward the remaining looped peak of the pair of opposite looped peaks increases monotonically, wherein, when the monotonically increasing distance is plotted as a function of distance from the one of the pair of opposite looped peaks at one end of the segment along the wave segment, the resulting curve includes an inflection point; and (ii) axial connectors joining adjacent expandable tubular members, replacing the guide wire with a pusher wire, and using the pusher wire to force the stent out of the catheter into the vascular site.

20. The method of claim 19, wherein radial expansion of the stent from its contracted to its expanded state is accommodated by movement of adjacent wave segment peaks away from one another, without significant change in the axial dimension of the stent.

21. The method of claim 19, each expandable tubular member being composed of a continuous wire element.

22. The method of claim 21, wherein the axial connectors are portions of the continuous wire element.

23. The method of claim 22, wherein the stent is cut from a tube.

24. The method of claim 19, wherein the axial connectors join one or more confronting peaks of adjacent tubular members.

25. The method of claim 19, wherein the neurovascular target vessel has an inner diameter less than about 8 mm.

26. The method of claim 19, wherein the catheter has a lumen inner diameter of 0.5 to 2 mm.

27. The method of claim 19, wherein the pusher wire is equipped at its distal end with a stabilizer that is engageable with the stent when forcing the same from the catheter.

28. The method of claim 19, wherein the stent in its contracted state has an inner diameter of between 0.5 and 2 mm, and a diameter in the expanded state of between 2-9 times that in the contracted state.

29. The method of claim 19, wherein, in the stent's contracted state, the sides have at least two inflection points.

\* \* \* \* \*